United States Patent
Wang et al.

(10) Patent No.: US 12,404,552 B2
(45) Date of Patent: Sep. 2, 2025

(54) METHODS OF SELECTING ANTIBODIES AND ANTIBODY FRAGMENTS

(71) Applicant: Allele Biotechnology & Pharmaceuticals, Inc., San Diego, CA (US)

(72) Inventors: Jiwu Wang, La Jolla, CA (US); Gerard G. Lambert, San Diego, CA (US); Nathan C. Shaner, San Diego, CA (US)

(73) Assignee: Allele Biotechnology & Pharmaceuticals, Inc., San Diego, CA (US)

( * ) Notice: Subject to any disclaimer, the term of this patent is extended or adjusted under 35 U.S.C. 154(b) by 579 days.

(21) Appl. No.: 15/212,215

(22) Filed: Jul. 16, 2016

(65) Prior Publication Data

US 2017/0044608 A1    Feb. 16, 2017

Related U.S. Application Data

(60) Provisional application No. 62/194,102, filed on Jul. 17, 2015.

(51) Int. Cl.
*G01N 33/68*    (2006.01)
*C12Q 1/6876*    (2018.01)

(52) U.S. Cl.
CPC ....... *C12Q 1/6876* (2013.01); *G01N 33/6854* (2013.01); *G01N 33/6857* (2013.01)

(58) Field of Classification Search
None
See application file for complete search history.

(56) References Cited

U.S. PATENT DOCUMENTS

| | | | |
|---|---|---|---|
| 2002/0006413 A1* | 1/2002 | Sobol | A61K 39/001139 424/277.1 |
| 2009/0111142 A1* | 4/2009 | Nielsen | C12N 15/1086 435/243 |
| 2011/0312505 A1* | 12/2011 | Reddy | G01N 33/6857 506/2 |
| 2012/0009221 A1* | 1/2012 | Hoerr | A61K 39/00 424/277.1 |
| 2013/0085072 A1* | 4/2013 | Bradbury | C12Q 1/02 506/1 |
| 2013/0259924 A1* | 10/2013 | Bancel | A61K 38/17 530/358 |
| 2015/0239990 A1* | 8/2015 | Dreier | C07K 16/462 435/69.6 |
| 2016/0159918 A1* | 6/2016 | Pillai | C07K 16/2803 424/133.1 |
| 2017/0212130 A1* | 7/2017 | Rout | C07K 16/44 |

OTHER PUBLICATIONS

Nakashima et al (Clinical Immunology and Immnopathology 80:204-10) (Year: 1996).*
Robins (Blood 114:4099-107) (Year: 2009).*
Sempowski et al (J. Immunol. 152:3606-14) (Year: 1994).*
Larimore et al (J. Immunol. 189:3221-30) (Year: 2012).*
Franceschi et al (PLOS One vol. 9 e105643; 13 pages). (Year: 2014).*
Fuji et al (Blood 113:4262-72) (Year: 2009).*
Coia, G. et al., Panning and Selection of Proteins Using Ribosome Display. Journal of Immunological Methods 254, 191-197, 2001.
Feldhaus, M.J. et al., Flow-Cytometric Isolation of Human Antibodies From a Nonimmune *Saccharomyces cerevisiae* Surface Display Library. Nature Biotechnology 21, 163-170, 2003.
Hamers-Casterman, C. et al., Naturally Occurring Antibodies Devoid of Light Chains. Nature 363, 446-448, 1993.
Irving, R.A. et al., Ribosome Display and Affinity Maturation: From Antibodies to Single V-Domains and Steps Towards Cancer Therapeutics. Journal of Immunological Methods 248, 31-45, 2001.
Mattheakis, L.C. et al., An In Vitro Polysome Display System for Identifying Ligands From Very Large Peptide Libraries. Proceedings of the National Academy of Sciences of the United States of America 91, 9022-9026, 1994.
Stanfield, R.L. et al., Crystal Structure of a Shark Single-Domain Antibody V Region in Complex With Lysozyme. Science 305, 1770-1773, 2004.
Warren, L. et al., Feeder-Free Reprogramming of Human Fibroblasts with Messenger RNA. Current Protocols in Stem Cell Biology, 1-27, 2013.
Reddy ST, Ge X, Miklos AE, Hughes RA, Kang SH, Hoi KH, et al. Monoclonal antibodies isolated without screening by analyzing the variable-gene repertoire of plasma cells. Nat Biotechnol. 2010; 28(9), pp. 965-969.

* cited by examiner

*Primary Examiner* — Christopher M Gross
(74) *Attorney, Agent, or Firm* — DUANE MORRIS LLP

(57) ABSTRACT

A multi-step method is disclosed for efficient selection of antibody or antibody fragments. In addition to the dramatically increased efficiency of finding antibodies against a given immunogen by the invented processes, the novel technology also differs from all previously known technologies in that the antibody or antibody fragments represent the most abundant antibodies induced by the immunogen, therefore having the highest potential of specificity and affinity. Utility of the invention can be found in virtually all areas that involve antibody or T cell receptor selection using any animal, against any immunogen.

19 Claims, 10 Drawing Sheets

1 - Ovotransferrin
2 - Ovalbumin
3 - Wheat gliadin
4 - Egg lysozyme
GFP - pulldown with EGFP-agarose (vector background)
input - total VHH library protein

| | A | B | C | D | E | F | G | H | I |
|---|---|---|---|---|---|---|---|---|---|
| 1 | N | Unused | Total | %Cov | %Cov(50) | %Cov(95) | Name | Species | Peptides(95%) |
| 2 | 1 | 63.8 | 63.8 | 81.55 | 81.55 | 81.55 | grp8_synthetic_30798;size=3; | | 117 |
| 3 | 1 | 0 | 63.8 | 81.55 | 81.55 | 81.55 | grp8_synthetic_794086;size=1; | | 117 |
| 4 | 1 | 0 | 63.8 | 81.55 | 81.55 | 81.55 | grp8_synthetic_765748;size=1; | | 117 |
| 5 | 1 | 0 | 62.84 | 83.33 | 83.33 | 83.33 | grp8_synthetic_201943;size=1; | | 118 |
| 6 | 1 | 0 | 62.82 | 79.17 | 79.17 | 79.17 | grp8_synthetic_294729;size=1; | | 116 |
| 7 | 1 | 0 | 60.91 | 76.79 | 76.79 | 76.79 | grp8_synthetic_516917;size=1; | | 116 |
| 8 | 1 | 0 | 60.91 | 76.79 | 76.79 | 76.79 | grp8_synthetic_464613;size=1; | | 116 |
| 9 | 2 | 48.67 | 54.76 | 75.63 | 75.63 | 75.63 | grp8_synthetic_840196;size=1; | | 52 |
| 10 | 2 | 0 | 50.76 | 75.63 | 75.63 | 75.63 | grp8_synthetic_224130;size=2; | | 57 |
| 11 | 2 | 0 | 54.76 | 75.63 | 75.63 | 75.63 | grp8_synthetic_103642;size=1; | | 52 |
| 12 | 2 | 0 | 52.76 | 63.13 | 63.13 | 63.13 | grp8_synthetic_838105;size=1; | | 51 |
| 13 | 3 | 30.71 | 30.71 | 43.78 | 43.72 | 43.72 | RecName: Full=Trypsin; Flags: Precursor | PIG | 52 |
| 14 | 4 | 16.88 | 39.23 | 68.75 | 68.75 | 68.75 | grp8_synthetic_90362;size=1; | | 30 |
| 15 | 4 | 0 | 39.23 | 68.75 | 68.75 | 68.75 | grp8_synthetic_753415;size=1; | | 30 |
| 16 | 4 | 0 | 39.23 | 68.75 | 68.75 | 68.75 | grp8_synthetic_721073;size=1; | | 30 |
| 17 | 4 | 0 | 39.23 | 68.75 | 68.75 | 68.75 | grp8_synthetic_710794;size=1; | | 30 |
| 18 | 4 | 0 | 39.23 | 68.75 | 68.75 | 68.75 | grp8_synthetic_62156;size=12; | | 30 |

FIG. 7.

| | A | B | C | D | E | F | G | H | I |
|---|---|---|---|---|---|---|---|---|---|
| 1 | N | Unused | Total | %Cov | %Cov(50) | %Cov(95) | Name | Species | Peptides(95%) |
| 2 | 1 | 123.44 | 123.44 | 79.37 | 79.37 | 79.37 | grp8_synthetic_224130;size=2; | | 206 |
| 3 | 2 | 39.83 | 72.02 | 72.5 | 72.5 | 72.5 | grp8_synthetic_858361;size=1; | | 76 |
| 4 | 2 | 0 | 80.02 | 72.5 | 72.5 | 72.5 | grp8_synthetic_134362;size=2; | | 81 |
| 5 | 3 | 35.6 | 35.6 | 43.72 | 43.72 | 43.72 | RecName: Full=Trypsin; Flags: Precursor | PIG | 42 |
| 6 | 4 | 21.41 | 82.47 | 75 | 75 | 75 | grp8_synthetic_360170;size=1; | | 89 |
| 7 | 4 | 0 | 86.94 | 62.5 | 62.5 | 62.5 | grp8_synthetic_319985;size=1; | | 104 |
| 8 | 4 | 0 | 68.37 | 68.12 | 68.12 | 68.12 | grp8_synthetic_270932;size=1; | | 69 |
| 9 | 5 | 17.09 | 35.27 | 76.79 | 76.79 | 76.79 | grp8_synthetic_90798;size=3; | | 28 |
| 10 | 5 | 0 | 35.27 | 76.79 | 76.79 | 76.79 | grp8_synthetic_794086;size=1; | | 28 |
| 11 | 5 | 0 | 35.27 | 76.79 | 76.79 | 76.79 | grp8_synthetic_765748;size=1; | | 28 |
| 12 | 5 | 0 | 35.27 | 76.79 | 76.79 | 76.79 | grp8_synthetic_294729;size=1; | | 28 |
| 13 | 5 | 0 | 35.27 | 76.79 | 76.79 | 76.79 | grp8_synthetic_201943;size=1; | | 28 |
| 14 | 5 | 0 | 34.84 | 76.79 | 76.79 | 76.79 | grp8_synthetic_357024;size=1; | | 23 |
| 15 | 5 | 0 | 34.02 | 72.02 | 72.02 | 72.02 | grp8_synthetic_516917;size=1; | | 27 |
| 16 | 5 | 0 | 34.02 | 72.02 | 72.02 | 72.02 | grp8_synthetic_464613;size=1; | | 27 |
| 17 | 5 | 0 | 33.62 | 76.79 | 76.79 | 76.79 | grp8_synthetic_834778;size=1; | | 27 |
| 18 | 5 | 0 | 33.27 | 70.24 | 70.24 | 70.24 | grp8_synthetic_84751;size=1; | | 22 |
| 19 | 5 | 0 | 33.27 | 71.43 | 71.43 | 71.43 | grp8_synthetic_793540;size=1; | | 26 |
| 20 | 5 | 0 | 33.27 | 70.24 | 70.24 | 70.24 | grp8_synthetic_792111;size=1; | | 22 |
| 21 | 5 | 0 | 33.27 | 71.43 | 71.43 | 71.43 | grp8_synthetic_780106;size=1; | | 26 |
| 22 | 5 | 0 | 33.27 | 73.81 | 73.81 | 73.81 | grp8_synthetic_710167;size=1; | | 25 |
| 23 | 5 | 0 | 33.27 | 70.24 | 70.24 | 70.24 | grp8_synthetic_662492;size=1; | | 22 |
| 24 | 5 | 0 | 33.27 | 70.24 | 70.24 | 70.24 | grp8_synthetic_503636;size=1; | | 22 |
| 25 | 5 | 0 | 33.27 | 71.43 | 71.43 | 71.43 | grp8_synthetic_475106;size=1; | | 26 |
| 26 | 5 | 0 | 27.31 | 76.79 | 76.79 | 76.79 | grp8_synthetic_668163;size=1; | | 23 |
| 27 | 5 | 0 | 27.31 | 76.79 | 76.79 | 76.79 | grp8_synthetic_24246;size=1; | | 23 |
| 28 | 5 | 0 | 26.06 | 72.02 | 72.02 | 72.02 | grp8_synthetic_79100;size=1; | | 22 |
| 29 | 5 | 0 | 25.31 | 64.88 | 64.88 | 64.88 | grp8_synthetic_838341;size=1; | | 22 |
| 30 | 5 | 0 | 25.31 | 64.88 | 64.88 | 64.88 | grp8_synthetic_753548;size=1; | | 22 |
| 31 | 5 | 0 | 25.31 | 64.88 | 64.88 | 64.88 | grp8_synthetic_613441;size=1; | | 22 |
| 32 | 5 | 0 | 25.31 | 64.88 | 64.88 | 64.88 | grp8_synthetic_538248;size=1; | | 22 |
| 33 | 5 | 0 | 25.31 | 64.88 | 64.88 | 64.88 | grp8_synthetic_519180;size=1; | | 22 |
| 34 | 5 | 0 | 24.06 | 60.12 | 60.12 | 60.12 | grp8_synthetic_232539;size=1; | | 21 |
| 35 | 5 | 0 | 23.31 | 58.33 | 58.33 | 58.33 | grp8_synthetic_770975;size=1; | | 16 |
| 36 | 5 | 0 | 23.31 | 57.65 | 57.65 | 57.65 | grp8_synthetic_335855;size=1; | | 16 |
| 37 | 5 | 0 | 23.31 | 58.33 | 58.33 | 58.33 | grp8_synthetic_201141;size=1; | | 16 |
| 38 | 5 | 0 | 23.31 | 59.52 | 59.52 | 59.52 | grp8_synthetic_119263;size=1; | | 20 |
| 39 | 6 | 14.8 | 40.02 | 76.73 | 76.73 | 76.73 | grp8_synthetic_629923;size=1; | | 34 |
| 40 | 7 | 13.7 | 31.86 | 66.05 | 66.05 | 66.05 | grp8_synthetic_679644;size=1; | | 20 |
| 41 | 7 | 0 | 31.55 | 70.99 | 70.99 | 59.26 | grp8_synthetic_446477;size=1; | | 19 |
| 42 | 7 | 0 | 30.68 | 66.05 | 66.05 | 59.26 | grp8_synthetic_44875;size=1; | | 19 |

FIG. 8.

METHODS OF SELECTING ANTIBODIES AND ANTIBODY FRAGMENTS

CROSS-REFERENCE TO RELATED APPLICATIONS

This application claims the benefit of U.S. Provisional Patent Application Ser. No. 62/194,102, filed Jul. 17, 2015 and titled "Methods of Selecting Antibodies and Antibody Fragments," the contents of which are incorporated herein in their entirety by reference.

FIELD OF THE INVENTION

The present disclosure relates to methods for selecting antibody and/or antibody fragments by identifying and functionally optimizing antibody genes and antibody-related protein fragments and sequences. More specifically, this invention relates to methods for preparing pharmaceutical batches for selecting cDNA or genomic DNA sequences from post-immunization animals that encode antibodies that recognize specific antigens. Further disclosed is a method of presenting immunogens to host animal cells to reduce the background antibody induction in the host, thereby simplifying the sequence-based antibody identification process. Additional aspects includes the establishment and utilization of variable gene sequences, structures, and antibody-antigen interaction databases for prediction of specific antibodies knowing only the antigen's structure, without the necessity of going through immunization or physical screening. Compared to other methods that are known in the art, the current invention provides a collection of closely related and sometimes alternative protocols and procedures that dramatically reduce the time, cost and effort involved in antibody identification and isolation. The invented procedures and processes can be used for isolating various forms of antibodies, other immune response molecules such as T-cell receptors, or antibody or receptor fragments such as the VHH fragments from camelid antibodies.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

Different types of molecules, such as RNA/DNA aptamers and peptides, have been developed as capture reagents with certain levels of success. Nonetheless, monoclonal antibodies (mAbs) are the most widely used reagents for specifically detecting and quantifying proteins due to their very high specificity and affinity. However, development of monoclonal antibodies by traditional hybridoma technologies is inefficient. In addition, the large size of monoclonal antibodies (150 kDa) may limit their use in cases where more than one binding reagent competes for space to recognize closely juxtaposed epitopes. Furthermore, production of monoclonal antibodies typically requires protein expression in mammalian systems, which adds significantly to the costs and instability of production. These limitations could arguably be the biggest hurdles to using monoclonal antibodies as capture reagents for a systematic study of the complete human proteome or for clinical applications of advanced proteomics.

Alternative formats of antibodies with sufficient specificity, affinity, and small size that can be more easily produced than monoclonal antibodies have been actively sought after in the last 2 decades. Among artificial antibodies or antibody fragments, a single-chain variable-fragment (scFv) is an often used format because it is easier to construct a library of scFv than other formats, such as Fab or Fab'. An scFv is only about 27 kDa and is comprised of only the light chain and heavy chain variable regions connected by a peptide linker. Since scFv retains the antigen-binding site of the variable regions of both antibody chains, it has the potential for having the specificity of an intact antibody. Besides, scFv can be expressed in yeast or bacteria with yields up to milligrams per liter.

Compared to the above mentioned artificial antibody derivatives (e.g. scFv, Fab, diabody), the N-terminal domain of heavy chain camelid antibodies, termed VHH domains (or $V_H H$, $V_{HH}$, nanobody, VHH antibodies), represents a fully functional, and structurally well characterized domain that is about only 12-16 kD in size, half that of scFv. It was first discovered that animals in the camel family (camel, llama, etc.) produce antibodies with no light chains (Hamers-Casterman et al., 1993). The only known species outside the camelidae family that has heavy chain-only antibodies is the nurse shark (Stanfield et al., 2004).

Monoclonal antibody generation relies on hybridoma technology or more recently, B-cell immortalization, or V-gene cloning by single-cell PCR. These processes invariably require high-throughput screening to determine antigen (also interchangeably referred to as immunogen, target) specificity, with considerable technical complexity. Different display systems for selecting antibody fragments using constructed libraries have been developed. Naïve or synthetic libraries can be screened with various display methods, often intended to avoid the use of animals. Phage display is probably the best known display method and is widely used for camelid antibody development. It is relatively simple to carry out because it uses *E. coli* and phage as the amplification system and carrier, respectively. Phage display has certain drawbacks, for example, upon expansion of the phage population, clonal diversity may be lost due to outgrowth of some of the phage clones. In contrast, a yeast library can be amplified 100-fold without noticeable loss of clonal diversity (Feldhaus et al., 2003). However, serious problems when using yeast-displayed scFv or Fab libraries have also been discovered, such as the instability of the libraries. It was observed that pooled plasmids of relevant libraries showed hypermutations in the yeast display vectors when stored in *E. coli* stocks at −80° C. One way of dealing with this is to store DNA stocks instead of bacteria stocks, which, unfortunately, would then require large scale transformation into competent cells every time the libraries need to be amplified. In vitro display methods have also been developed with the aim of avoiding cellular systems thereby increasing the library degeneracy. Such displays include polysome display (Mattheakis et al., 1994), ribosome display (Coia et al., 2001; Irving et al., 2001), and central display by the Allele Biotechnology team (J Wang, supported by NIH grant 1R43CA89990), but these systems are less mature compared to phage and yeast display systems and are seldom used for large scale antibody development projects. On the other hand, while there have been many reported examples of successful use of synthetic or naïve antibody gene libraries, the typical diversity of these libraries is still much smaller than the pools of antibodies in immunized animals, limiting their capacity to produce high quality antibodies against certain antigens.

SUMMARY OF THE INVENTION

Accordingly, to address these deficiencies, the present disclosure provides methods and compositions for generating useful antibodies or antibody fragments with unprecedented ease and efficiency. These new methods can be applied to finding other affinity molecules such as T cell receptors. However, for simplicity the disclosure will use antibody as the subject. Even though antibodies are commonly referred to as a class of proteins that are composed of typical antibody chains, sometimes their fragments can function as complete antibodies. Therefore, throughout this disclosure, antibodies, antibody fragments, or antibody regions are sometimes referred to separately to emphasize their difference, and sometimes interchangeably for simplicity. In one embodiment, monoclonal antibodies or antibody fragment encoding genes are determined by highly parallel sequencing (also termed next-generation sequencing, deep sequencing). The use of the exemplary methods and compositions described herein result in significantly improved efficiency over previously reported antibody gene isolation methodologies and overcame a previously unsolved problem matching possible antibody encoding genes and the actually existing antibodies.

Genomic DNA (gDNA) or mRNA pools are isolated from animals after immunization regimen appropriate for the chosen type of host animal; either gDNA or cDNA (reverse transcribed from mRNA) is then sequenced by the deep sequencing methods known in the art; antibodies or antibody fragments composed of amino acid chains is sequenced by any of the peptide or polypeptide sequencing methods such as the MASS spectrometry (MASS spec), more specifically, a method such as MALDI-TOF.

In one embodiment, the present disclosure provides a method of obtaining DNA sequences that encode antibodies or antibody fragments comprising 1) immunize the animal of selected species with antigens, such as recombinant proteins, synthetic peptides, haptens, special modification groups found on DNA, RNA, or proteins, etc. In one particular embodiment, the antigen is presented in cells originated from the same animal or an animal of the same species to be used for immunization, thereby reducing background antibodies (defined as antibodies generated by the host animal against carrier molecules, linkers, conjugates, etc. that are co-introduced to the animal during immunization but are not the actual immunogen). In one embodiment, cells are first isolated from the animal to be immunized and established as expandable cell lines in vitro. In one example presented herein, cells were isolated from ear tissues of a llama and transformed into stable cell lines by transfecting a transforming factor such as an hTERT gene, H-rasV12, or an sv40 large-T antigen (FIG. 1). The cDNA encoding a human protein as target is introduced into the cells so that the llama cells will present the human protein as immunogens once introduced back into the host animal. In one embodiment, said cells are transfected with mRNA encoding the immunogen proteins in order to obtain a high level of expression without further cell selection. Thus, instead of expressing and purifying the human protein as antigen, the cells now expressing the human gene from transfected mRNA (or cDNA) can be injected into the animal; 2) after appropriate immunization regimen, blood of the immunized animal is drawn, then lymphocytes are enriched and isolated from the blood; 3) gDNA and/or mRNA from lymphocytes are then extracted, mRNA further converted into cDNA; 4) gDNA and/or cDNA pools are sequenced through a protocol that can generate sequence information of DNA molecules in highly parallel fashion; 5) sequences of the highest abundance are selected and the antibodies or antibody fragments they encode serve as candidates of specific antibodies against the immunogens.

In one detailed embodiment of antigen presentation, the inventor created antigen-carrying vesicles by first transfecting cells isolated from the host species by optimizing transfection conditions, mRNA sequence and structure including 3' UTR, sometimes with help of expressing enhancing long noncoding RNAs (lncRNAs), and using the whole cell post-transfection for immunization by injecting about 1-10 million cells; alternatively, cells are broken up by sonication or passing through a pressurized channel such as a syringe, cell membranes are then collected, and used for immunization. The use of host cell-based antigen presentation in the discovered process solved previously unsolved problems of immunizing animals with insoluble membrane proteins.

Abundance ranking has been previously described by others in determining candidates for immunogen-induced antibody genes created in B cells of mouse (Reddy et al. 2010). Furthermore, soon after the inventors of the current invention filed the first provisional US patent application using abundance ranking Fridy et al reported isolating of camelid antibody fragment (termed nanobodies in that publication) by ranking the abundance of cDNAs encoding antibody genes post-immunization. In contrast, in one additional embodiment, the present disclosure provides a method of obtaining gDNA clones, instead of cDNAs that encode an antibody or antibody fragment comprising 1) immunizing the animal of selected species with target antigens as described above; 2) after appropriate immunization regimens, drawing blood from the immunized animal, the antibodies from the blood are then enriched (e.g. through protein A/G affinity chromatography) and isolated (e.g. through antigen-specific affinity chromatography and immobilized binding); 3) analyzing the sequences of the isolated antibody or their fragments through a protein sequencing procedure that can generate amino acid compositions and sequence information; 4) identifying the potential antibodies or antibody fragments of the highest abundance as antibodies specific against the immunogens.

In another embodiment, the present disclosure provides a method of obtaining gene (gDNA or cDNA) clones that encode an antibody or antibody fragment specific against an antigen comprising combining the results from both the gDNA/cDNA sequencing and the polypeptide sequencing. Such combination involves using DNA and polypeptide samples from the same immunized animal to facilitate the identification of antibody or antibody fragment encoding genes, then to identify potential antibody or antibody fragments that can recognize the immunogens, which has not been previously taught by workers in the antibody development field. During the disclosed process of gene assembly, sequences of gene fragments obtained through deep sequencing are assembled into continuous DNA sequences encoding a complete functional antibody domain such as a variable region, V genes, VHH genes in particular. When assembling V genes, the protein sequence information obtained with the enriched and purified antibodies is used as reference. To obtain antigen-specific antibody amino acid sequences, antibodies from the serum, spleen, or bone marrow are enriched by affinity binding to antigen-presenting solid support such as beads, washed to remove non-specific or low-affinity binders. The bound antibodies with desired affinity are then released, further purified if necessary, then collected for protein sequencing, e.g. by MASS spectrometry.

In another embodiment, a pool of antibodies is generated from a pool of antibody-encoding gDNA or cDNA from immunized animal by in vitro translation or transforming into a host cell such as a bacterium or yeast. The advantage of this route is the antibodies can be purified via affinity tag added during DNA cloning, resulting in less background proteins. More specifically, as demonstrated in one of the examples in this disclosure, nano antibody genes from an immunized library against were cloned by common molecular biology methods from blood onto a plasmid vector, which added a 6×His tag sequence, then transformed into E. coli. Recombinant proteins were then isolated and bound to immunogen.

In one embodiment, the source of the antibody is a camelidae animal, in another embodiment, the source is a nurse shark, and in another embodiment the antibody is a heavy-chain only antibody. In one aspect, the VHH domain of the antibody heavy chain from a camelid animal, such as a camel, a llama, an alpaca, or from a nurse shark, is the preferred antibody fragment(s). The gDNA or cDNA clones encoding such antibodies or antibody fragment identified by the methods disclosed hereby are embodiments of the current invention.

In one embodiment, the exemplary VHH-encoding sequences, which are on one continuous exon in llama, can be identified in the genome of lymphocytes. After immunization, the antibody variable genes such as the VHH genes often undergo changes that result in production of antibodies specific against the immunogens. A collection of lymphocyte genomes can be subject to parallel sequencing. In practice of the current invention, the VHH encoding gDNA region can be amplified by polymerase chain reaction (PCR) before sequencing. Alternatively, the VHH-encoding gDNA may be sequenced directly through whole genome sequencing without PCR amplification.

In one particular embodiment, the heavy-chain-only antibodies from camelid animals or nurse sharps are isolated by protein A and or protein G columns, or by size exclusion chromatography or other techniques known in the art, digested by appropriate protease(s), then subject to MASS spec polypeptide sequencing. All peptide fragments of the isolated antibodies are identified by MASS spec to obtain their precise molecular weights and possible amino acid compositions.

In another aspect, the current invention discloses that information of VHH antibodies, such as their sequences, structural features, interaction with their known binding sites on specific antigens, epitopes, the affinities of the bindings, and the change of affinities and specificities when limited mutations are introduced, can be organized into a database from which new VHH antibodies, or other antibodies or antibody fragments of similar size and structures of VHH, can be developed through bioinformatics. Therefore, the current invention also provides novel methods of identifying useful antibodies or antibody fragments without the need to go through physical display or other in vitro screening.

In one embodiment, the variable regions of antibody heavy chains or light chains from an immunized animal, e.g. mouse, rat, rabbit, goat, llama, etc., are amplified from a gDNA or cDNA library made from lymphocytes isolated from the bone marrow or circulating blood. The resulting variable region library is then sequenced and the sequences belonging to the top 1%, 5%, 10%, 15%, 20% or even 25% abundance are selected as genes encoding candidate immunogen-specific antibodies. The assembly of the complete V genes from either the heavy or the light chains, as well as the complement of the heavy and light chains, can be facilitated by protein sequencing conducted using enriched and antigen-affinity isolated antibodies. In a related procedure, the variable regions of heavy and light chains from the same immunized animal can be predicted and theoretically matched by combining DNA and protein sequencing. Similarly, the variable regions of T cell receptors that recognize a particular target can be selected.

BRIEF DESCRIPTION OF THE DRAWINGS

The invention will now be described in relation to the drawings in which:

FIG. 7. Sample mass spectrometry search results from mWasabi VHH library protein pulldown, band A (high molecular weight).

FIG. 8. Sample mass spectrometry search results from mWasabi VHH library protein pulldown, band B (low molecular weight).

DETAILED DESCRIPTION OF THE INVENTION

Figure 1:
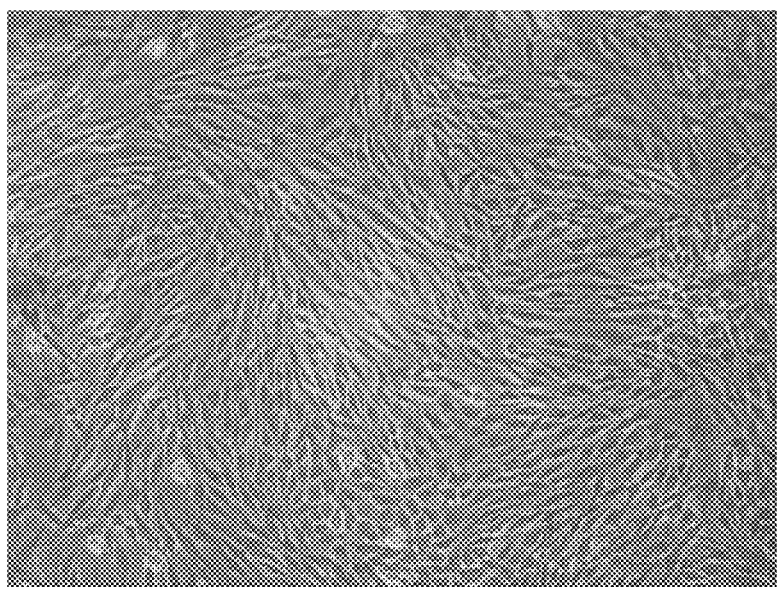
FIG. 1. Isolated llama cells as a self-cell platform for antigen presentation. The 10× bright field image shows one example of cells isolated from a llama used for VHH antibody generation. The cells were further developed into transformed cell lines and banked for repeated use as antigen presenting cells.

When describing the present invention, all terms not defined herein have their common meanings as recognized In the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention.

In one aspect, the current invention relates to antibody selection by sequencing. The recent advances in complete genome-scale sequencing technologies have enabled finding genetic information with efficiency and accuracy. The current invention focuses on implementation of deep sequencing-based and sequence database-supported methods for identifying and generating antigen-specific antibodies or antibody fragments. Variable region (V) genes within antibody gene families can be sequenced by next-generation sequencing using, for example, a 454 format, illumine systems, or other platform technologies for highly parallel or "deep" sequencing, after immunization. Particularly, the instant inventors describe a method of directly sequencing the gDNA region that encode a single domain antibody fragment that is fully capable of binding a target. The target may be a polypeptide, a peptide, a hapten, etc. Bone marrow plasma cells (BMPCs) can be used as source for V gene repertoire. While BMPCs in mice or rabbits are reasonably amenable to isolation, retrieving them from larger animals such as llama requires surgical procedures for which the cost and complexity shall make the process unpractical. The current invention discloses the use of blood cells collected from immunized animals as the source of the gene pool for sequencing. Sequencing results generated using PCR-amplified gDNAs or cDNAs may be biased when the percentage of each sequence in the pool is determined. In one embodiment, the antibody genes can be sequenced directly without PCR amplification, so that PCR-generated bias will not be carried into percentage calculations.

There has not been any attempt to use highly parallel sequencing to analyze the genomes of lymphocytes for the purpose of isolating antigen-specific antibodies because it is not known if there is any correlation between the percentage of an antibody gene on the chromosomes in a lymphocyte pool and the specificity of the antibody against the immunogen. The current invention describes a process of choosing immunogen-specific antibodies or antibody fragments from genome sequences, preferably without any PCR-amplification.

Even with deep sequencing's capability to obtain billions of nucleotide sequences, it is sometimes still difficult to assemble the complete sequence of each clone (defined as one continuous DNA molecule), particularly when the sequence to be assembled is longer than the limit of a single "read" by the equipment used, e.g. about 400 nucletodies or nts, nt, per common read. The current invention teaches a highly unique and previously unavailable method by combining sequence information of both the possible V genes predicted by deep DNA sequencing with polypeptide sequencing through MASS spec. In one example, all proteins from serum samples are affinity purified through protein A or protein G (or combined) chromatography. MASS spec sequencing can be performed at this stage. Alternatively, the antibodies can be further purified by antigen-specific chromatography. For example, an antigen protein is immobilized on beads through conjugation or affinity-binding, then the antibody pool is applied to make contacts with the immobilized antigens, the unbound antibodies then washed away, and the bound antibodies recovered into solution by changing pH or other binding environment factors. The purified antibodies are then subject to MASS spec sequencing or other polypeptide sequencing procedures. By knowing what peptide fragments are present in the immunized animal's blood and what possible fragments are predicted to be gene-encoded from highly parallel DNA sequencing, a skilled worker in the art can now have a much improved chance of identifying the actual immunogen-induced antibodies produced by the host animal.

The aspect of combining DNA and protein sequencing results in deciding the presence and percentage of presence of antibody genes in a library can be applied to choosing VHH antibody fragments of camelid or nurse shark heavy-chain-only antibodies. It can also be applied to V genes of the heavy chain and light chains of a typical 4-chain antibody. This new methodology and its principle can further assist matching V genes of the heavy chain and light chains. In one embodiment, the presence and the percentage of a VHH fragment within a pool is used to determine whether a VHH gene, identified from sequencing the gDNA or cDNA pool from an immunized llama, is a high quality candidate antibody gene. In another embodiment, the presence and the percentage of a heavy chain V gene and light chain V gene within their respective pools is used to determine whether a pair of the V genes, identified from sequencing the gDNA or cDNA pools from an immunized animal and assembled by referring to protein sequencing by MASS spec, is an a high quality candidate antibody heavy chain and light chain V gene pair.

Even though the current invention particularly relates to methodologies of finding variable regions of various antibody genes without the need of traditional expression and display methods, in one additional embodiment, the sequences identified by the herein disclosed bioinformatics methods can be cloned into appropriate vectors, such as plasmid, phagemid, viral vectors, etc., for expression and testing the antibodies in target recognition and other properties such as stability, affinity, or specificity.

One aspect of the current invention relates to the additional maturation of the selected antibodies through protein engineering. As a specific aspect of the current disclosure, a skilled worker can perform computational structure prediction using at least one platform (e.g. I-TASSER, PHYRE, Rosetta) based on the knowledge of a V gene, such as that encoding a VHH domain (also termed nano-antibodies or nAbs by the current inventors) from camelid antibodies. In one aspect, arginine side chains that are predicted not to participate in epitope binding or protein folding are identified using the predicted structure(s). As another example, site-directed mutagenesis can be used to substitute serine for any extraneous cysteine residues, and lysine for any non-essential arginine residues, in order to reduce protein aggregation and to facilitate conjugation onto solid supports or fluorophore via amine-reactive chemistry. One can then clone the resulting open reading frame of the antibody fragment into a common $E.\ coli$ expression vector with a His6 purification tag, for instance, and express it in $E.\ coli$ then purify; multiple monoclonal nAbs can then be selected against each antigen for further characterization and development.

From an accumulated database of VHH structures and corresponding binding epitopes and affinities, a database can be built to record such correlations. Such a database can also integrate structural studies of antibody-antigen pairs by co-crystallization or complex NMR analysis. In one further embodiment of the current invention, antibody domains can be predicted to bind to particular targets based on accumulated structure information and antibody-antigen co-structure and interaction information. This aspect of the current invention is particularly useful when the prediction is to be made for simple antibody fragments such as VHH, which is as small as 12-16 kD, of just about 100 amino acids. Ultimately, this method can remove the need for immunization and sequencing in the preparation of batch pharmaceuticals for the purpose of administration and therapeutic treatment.

EXAMPLES

Example 1—Immunogen Preparation

Llama tissues were obtained from a young male adult by surgery; cells were isolated by dissociation from tissues and maintained in culture under common conditions (FIG. 1). Cell populations as defined by different morphologies were separated and expanded. In some populations, an expression plasmid encoding a transforming factor were transfected into the cells so that the cells became transformed to become a permanent cell line. Antigen proteins are expressed from transfected plasmids, linear DNA template, or preferably mRNA. Plasmid constructs serving as the basis for generating antigen protein expressing mRNA were made as described previously by the inventor's group (Warren and Wang, 2013). For example, human CD34 cell surface protein encoding cDNA was first cloned into pIVT (Allele Biotech), which was used to produce in vitro transcription (IVT) template. Synthetic mRNA was generated in IVT reactions using a 4:1 ratio of ARCA cap analog to GTP to generate a high percentage of capped transcripts. A 20% substitution of 5 m-CTP for CTP and 2-Thio-UTP for UTP in the nucleotide triphosphate (NTP) mix was employed to reduce the immunogenicity of the RNA products. Cap analog and modified NTPs were purchased from Trilink Biotechnologies. A 2.5×NTP mix was prepared (ARCA: ATP:GTP:C:5m-CTP:UTP:2-Thio-UTP at 15:15:3.75:3: 0.75:3:0.75 mM). Each 20 uL IVT reaction comprised 8 uL NTP mix, 2 uL 10×T7 Buffer, 8 uL DNA template and 2 uL T7 enzyme (Promega). Reactions were incubated 4-6 hours at 37° C. and then treated with 1 uL RNAse-free DNase for a further 30 minutes at 37° C. before being purified on a spin column, the RNA product being eluted in a volume of 80 uL. Add 3 uL Antarctic Phosphatase for 10 min to remove immunogenic 5' triphosphate moieties from uncapped transcripts and 10 uL of reaction buffer (NEB). Phosphatase reactions were incubated for 30 minutes at 37° C. and the IVT products were re-purified if necessary.

Llama cells were cultured at about 30% confluency in DMEM/F12. Transfections commenced the day after seeding of target cells, and were repeated at 24-hour intervals for the durations planned. An RNA dose of 1200 ng was delivered to each well of a 6-well plate using RNAiMAX (Invitrogen) 4 hours prior to daily media change, except as otherwise noted. RNAiMAX-based transfection cocktails were made up by diluting 100 ng/uL RNA 5× in calcium/ magnesium-free DPBS and 5 uL of RNAiMAX per ug of RNA 10× in the same diluent, pooling to produce a 10 ng/uL RNA/vehicle suspension and dispensing to culture media after a 15-minute room temperature incubation.

The expression level of the transfected cDNA or mRNA can be monitored with a co-transfected or fused fluorescent protein gene, e.g. mNeonGreen (Allele Biotech). The cells are cultured 2-3 days post the last transfection, collected, and used for immunization. As an example, RNA molecules encoding Epithelial cell adhesion molecule (EpCAM) protein and a C-termial fusion to GFP or mNeonGreen were transfected into large-T antigen transformed llama fibroblasts and the expression of the fusion could be monitored by visualizing a fluorescent ring around the cell surface.

Example 2—Isolation of gDNA or Create cDNA from Circulating B Cells

Figure 2:
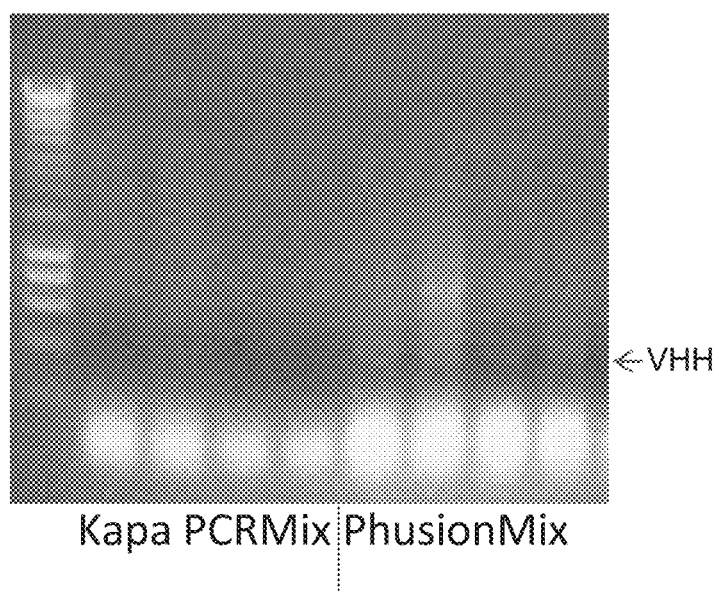
FIG. 2. gDNAs encoding llama VHH fragment were amplified Examples of amplified gDNA libraries are shown as bands in an agarose gel. The first lane is a size ladder. Lane 2-5 shows PCR reactions using Kapa master mix (Kapa); Lane 6-9 shows PCR results using Phusion PCR enzyme (NEB). The VHH encoding gDNA band is about 400-500 bp, as indicated on the right hand side.
Figure 3:
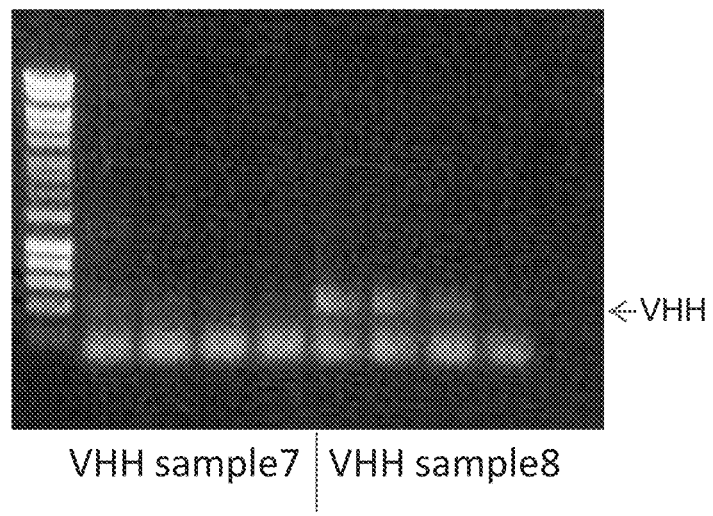
FIG. 3. cDNA encoding llama VHH fragment were amplified Examples of amplified cDNA libraries are shown as bands in agarose gel electrophoresis. The first lane is a size ladder. Lane 2-5 shows PCR reactions with one VHH sample cDNA; Lane 6-9 shows PCR results using another VHH cDNA. The PCR program is 95 C 2 min; 98 C 15 sec, annealing 15 sec, 72 C 30 sec for 30 cycles; 72 C 2 min. For annealing, lanes 2 and 6: 58.1 C; lanes 3 and 7: 60.8 C; lanes 4 and 8: 63.5 C; lanes 5 and 9: 66 C. The VHH encoding gDNA band is about 400-500 bp, as indicated on the right hand side.

After immunizing llama 3-6 times with antigens in the range of millions of cells (or 1 mg of purified protein antigens), with ~2 weeks interval, blood was collected 4 days after each injection to monitor the expected immune response by ELISA. Four days after the last immunization, 500 ml blood was collected, lymphocytes were enriched and selected from the blood with Lymphoprep (Axis-Shield PoC, Oslo, Norway). gDNA was purified from lymphocytes using Allele Biotech's SurfaceBind gDNA purification kit (FIG. 2). mRNA was purified from lymphocytes using Allele Biotech's SurfaceBind RNA purification kit for cDNA library construction (FIG. 3). cDNA library with mRNA from the previous step was synthesized using a SuperScript II First Strand Synthesis System (Thermo-Fisher) according to the manufacturer's instructions. 20 ug of purified mRNA and 8 ug oligo dT (Allele Biotech) was used for first strand synthesis. Double strand cDNA or gDNA was produced by PCR with primers previously designed for llama VHH amplification. The cDNA library was digested with appropriate restriction enzymes, ligate to linearized vector plasmid.

Example 3—Deep Sequencing of gDNA or cDNA from Immunized Pymphocytes

The regions of VHH encoding sequences from gDNA or cDNA collection in cloned pools were sequenced by any of the available nextgen sequencing platforms, e.g. HiSeq, IronTorrent, 454, and any of the newer technologies still in development. When appropriate coverage of sequences is afforded, it is possible to directly sequence isolated gDNA without first amplifying the VHH region. The sequencing results were then analyzed bioinformatics software to identify the VHH sequences, and the percentage of each sequence within the pool was calculated.

Example 4. Mass Spectrometry Analysis of Isolated Antibodies

The serum layer of the collected blood was separated from the cells by EDTA treatment and sedimentation. IgG antibodies were enriched with protein A/G beads, then further purified with CD34 expressing cells or conjugated solid support. The resulting proteins were analyzed by mass spectrometry to identify all potential protein sequences, focusing on those of VHH potentially against CD34. The results were combined with DNA deep sequencing to determine which sequences encode the best candidates of anti-CD34.

Example 5. VHH Antibody Cloning from gDNA

As described above, traditionally, libraries of VHH domain sequences from immunized camelids have been constructed by PCR-amplifying cDNA from peripheral blood lymphocytes. However, because the genomic DNA (gDNA) loci encoding VHH domains do not contain any introns, it is possible to generate equivalent VHH domain sequence libraries by PCR amplifying gDNA instead. This method has several advantages, including greater ease of extracting gDNA from peripheral lymphocytes compared to extracting mRNA, and much greater long-term stability of extracted gDNA compared with RNA, allowing more effective archiving of materials.

Figure 4:
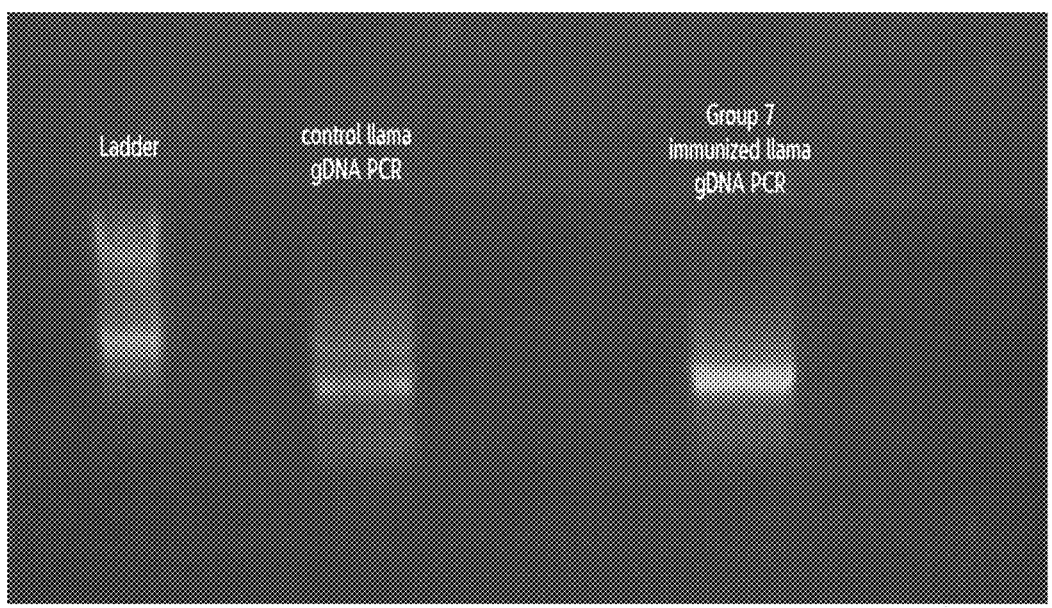
FIG. 4. VHH sequence amplified from llama lymphocyte gDNA after immunizing a llama with a group of proteins including mWasabi.

To demonstrate that VHH regions could be amplified from gDNA similarly to cDNA, we collected whole blood from an immunized llama. This blood was then fractionated by centrifugation and the white cell fraction isolated. We then extracted gDNA from these white cells using silica column purification. The gDNA was amplified using a set of universal VHH-region primers designed based on our own extensive database of VHH sequences previously cloned from approximately 5 different immunized llamas. See in FIG. 4, the amplified VHH region from gDNA.

To verify that amplified gDNA indeed contained VHH domain sequences, we used Illumina MiSeq to sequence a similar DNA band amplified from a new immunized llama. This sample was multiplexed along with several other cDNA-derived samples in the same sequencing run. After post-processing to select for only full-length VHH sequences, the gDNA sample yielded 67,383 VHH sequences that could be grouped into 51,845 clusters with >95% sequence identity. Of the full-length gDNA-derived sequences, >34% match with >90% sequence identity to sequences in a cDNA-based library sequenced from the same llama, with the most highly represented sequences being highly likely to be present in both samples. This indicates that gDNA-derived VHH libraries are functionally equivalent to cDNA-derived VHH libraries. These gDNA libraries are suitable for bioinformatic data mining and for use as databases for mass spectrometry (see below).

Example 6. VHH Protein Library Screening with Mass Spectrometry

As described in the above text, a previous method of identifying VHH antibodies against an immunogen through bioinformatics was to sequence VHH domains of a cDNA library and chose the candidates by percentage ranking, based on the theory that antibodies specific to recent immunogen(s) should be of higher percentage than those produced by circulating B cells prior to immunization.

We invented a method of combining antibody-coding gene ranking with antibody protein information. The antibody proteins can be isolated from blood or bone marrow from immunized llamas, as shown in the above Example 4. As a cleaner, faster, and more specific method of screening VHH libraries, we constructed "synthetic" VHH protein libraries by inserting cDNA- or gDNA-derived VHH sequences from immunized llama peripheral blood lymphocytes into an *E. coli* expression vector. This vector was designed in-house and utilizes a constitutive promoter, eliminating the requirement for induction, and also encodes an N-terminal 6xHis tag for immobilized metal affinity chromatographic (IMAC) purification of the expressed protein. DNA ligation reactions were transformed into ultracompetent *E. coli* and grown in liquid culture overnight, supplemented with antibiotic after an initial 1 hour recovery. A small fraction of the transformed library was also plated, allowing us to estimate the diversity of the library by calculating the total number of transformants. Typically this process yielded 1 to 2 million clones, sufficient to sample a high diversity of VHH sequences. We then purified plasmid DNA from the overnight liquid culture of library transformants to produce a VHH expression plasmid library.

A VHH protein library was produced by transforming the VHH plasmid library into NEB SHuffle strain *E. coli* (New England Biolabs), which contain modifications that allow disulfide bond formation in the cytoplasm. After 1 hour recovery at 30° C., the transformed cells were grown for 4 to 8 hours in 10 ml 2xYT broth supplemented with antibiotic. This culture was then transferred to 500 ml of 2xYT broth supplemented with antibiotic and the culture was grown at 30° C. for 24-36 hours. The cells were then harvested by centrifugation, lysed by sonication, and the 6xHis-tagged VHH protein purified on an IMAC column. Eluted protein was buffer exchanged using ultrafiltration into PBS pH 7.2 for subsequent steps. When visualized on an SDS-PAGE gel with Coomassie staining, purified VHH library protein typically formed a broad distribution of bands with apparent molecular weights centered around ~20 kilodaltons (kD) (FIG. 5), as expected for ~12-15 kD VHH protein with a ~7 kD N-terminal 6xHis tag and linker.

We immobilized each antigen used for immunization on 2% crosslinked glyoxal agarose beads (Agarose Bead Technologies). In parallel, we produced control agarose by blocking the glyoxal reactive sites on identical beads—these control beads were used to pre-clear the VHH library protein of nonspecific binders. The VHH library protein was incubated with control agarose prior to all subsequent experiments. We incubated 200 to 1000 µl of each agarose-immobilized antigen in 10 to 20 ml of PBS pH 7.2 containing a total of 10 to 20 mg of purified VHH library protein for 2 hours at room temperature with end-over-end tumbling. After incubation, the agarose was applied to a gravity column and the flow-through was collected for subsequent rounds of screening. The agarose was then washed with approximately 50 bed volumes of PBS pH 7.2, then with 10 to 20 bed volumes of 20 mM Tris-HCl pH 7.5+1.5 mM $MgCl_2$ to remove non-specifically bound protein, and then again with 10 bed volumes of PBS pH 7.2. The specifically-bound VHH protein was then eluted with 200 mM glycine pH 2.5 or pH 2.0 and immediately neutralized with concentrated Tris base. Eluted protein was run on SDS-PAGE and stained with Coomassie dye.

Figure 5:
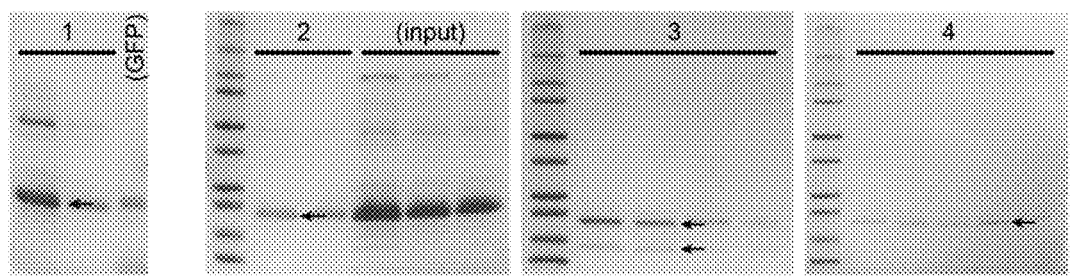
FIG. 5. Eluted VHH proteins from columns containing immobilized egg and wheat antigens, along with an immobilized GFP control pulldown.

Because the plasmid used as the source of the plasmid vector backbone for library generation contains the VHH antibody "GFP-nAb" which recognizes the fluorescent protein GFP, a small amount of this antibody is present as a minor contaminant in most of our VHH library protein preparations. This serves as a positive control for VHH binding, as it is possible to isolate the GFP-nAb protein using GFP immobilized on agarose, as we have done with the other antigens. FIG. 5 includes a typical result from this positive control pulldown.

Figure 6:
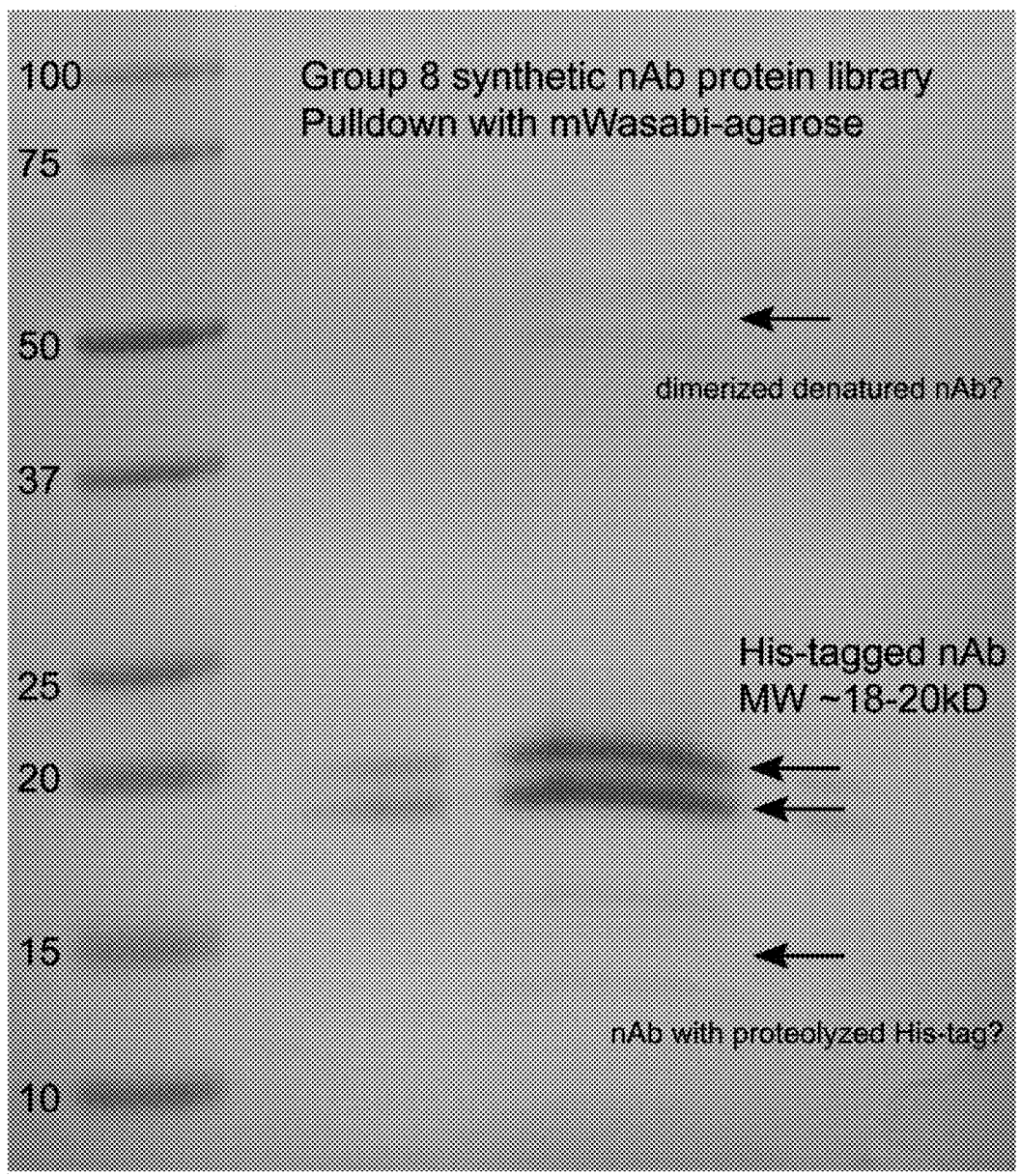
FIG. 6. Eluted VHH proteins from an immobilized mWasabi column.

The results of VHH protein library pulldowns using the antigens Ovotransferrin (chicken egg), Ovalbumin (chicken egg), lysozyme (chicken egg), gliadin (wheat gluten), and mWasabi (a fluorescent protein) are shown in FIG. 5 and FIG. 6. Bands that were subsequently excised for mass spectrometric analysis are indicated with arrows.

To produce a sequence database for use in mass spectrometric analysis, we PCR-amplified VHH libraries from identical samples to those used for protein library construction, adding adapter sequences for Illumina MiSeq paired-end sequencing. Samples were sequenced with 2x250 bp reads, typically generating around 1 million full-length VHH sequences per sample. Post-processing of the sequencing included assembly of paired-end reads into full-length VHH sequences (rejecting all that did not have sufficient overlap to assemble a full sequence), filtering out non-VHH sequences (typically a few percent of total reads), and removing short sequences (typically a few percent of truncated VHH sequences). We then generated peptide sequences corresponding to each unique MiSeq library clone and appended the N- and C-terminal vector-derived amino acids (including the 6×His tag and linker) to each, producing a sequence database that represented the full-length peptide sequences of all VHH library proteins for each sample. The use of a "synthetic" protein library rather than llama serum enabled the determination of the exact full-length sequence of all proteins, eliminating unknown N- and C-terminal sequences for each antibody clone. This greatly facilitated identification of proteins using mass spectrometry by eliminating many contaminating components and by increasing the number of unique, identifiable peptides for each clone.

VHH protein bands were excised from SDS-PAGE gels for each VHH library protein pulldown on immobilized antigen. These bands were then sent to the UC San Diego Biomolecular and Proteomics Mass Spectrometry facility for in-gel trypsin digest followed by reverse phase liquid chromatography separation coupled to Triple TOF mass spectrometry. The resulting ion masses were then searched against an in silico-digested version of the appropriate VHH library, generated as described above. Typical results are shown in FIG. 7 and FIG. 8 for mWasabi VHH bands.

Figure 9:
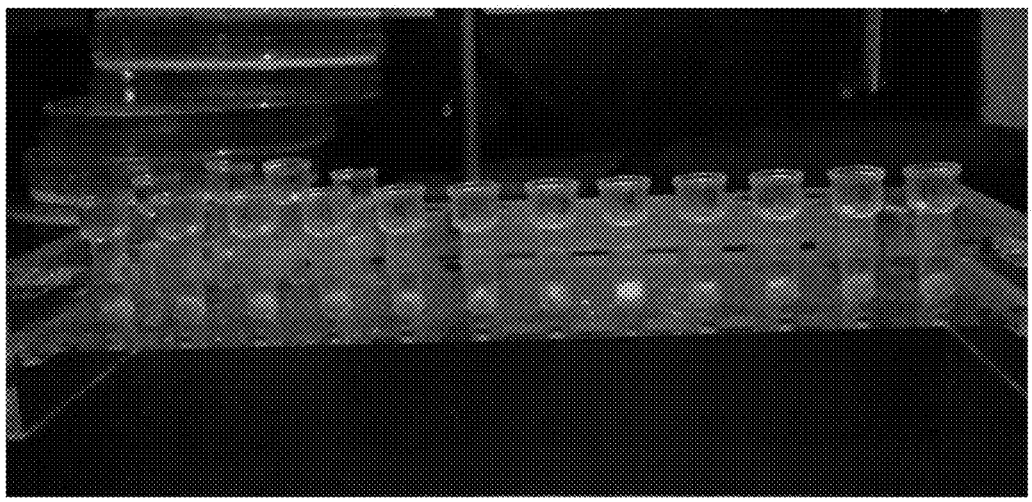
FIG. 9. Small-scale test of mWasabi VHH clones identified via mass spectrometry of VHH library protein pulldown bands. VHH protein was immobilized on IMAC resin and incubated with untagged mWasabi protein. After several washes, the fluorescence was visualized under blue excitation.
Figure 10:
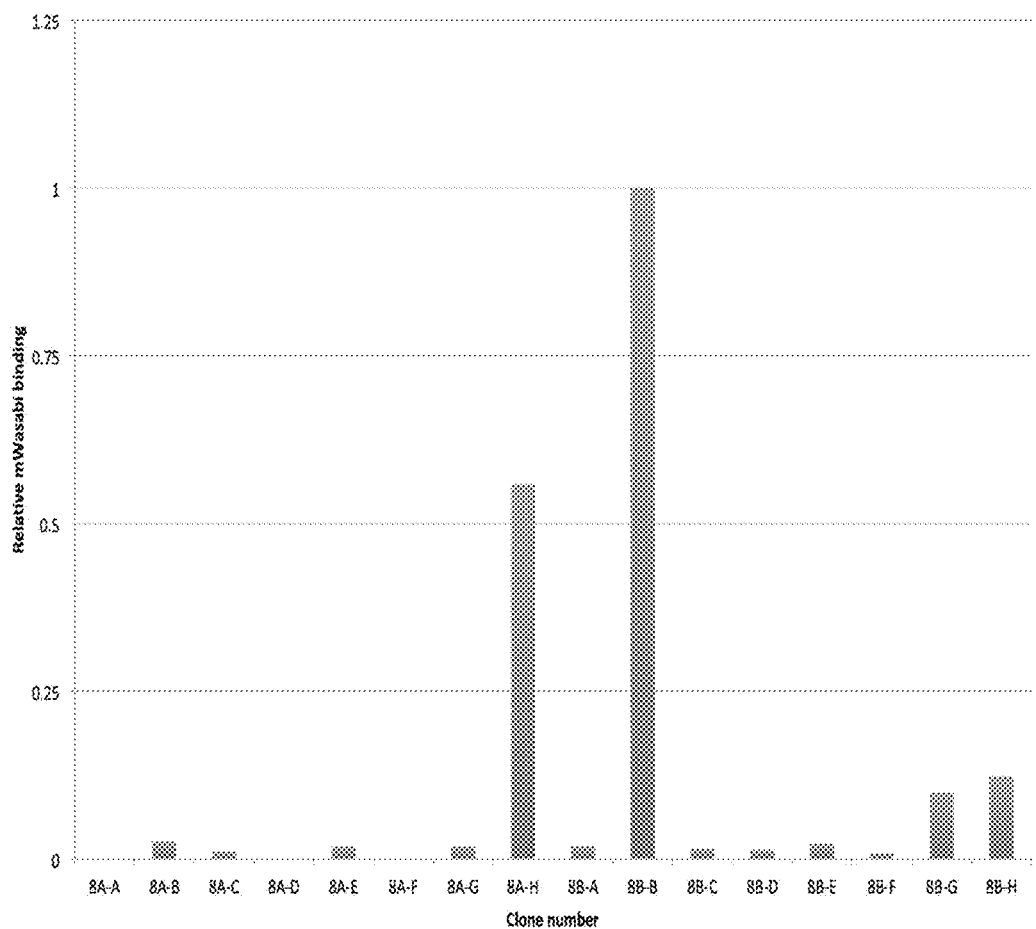
FIG. 10. Quantitation of mWasabi protein eluted from each of the columns shown in FIG. 9. Four clones show strong binding.

Example 7 Identifying VHH Antibodies after Combining DNA and Protein Sequence Information We then synthesized the VHH DNA sequences corresponding to the top clones identified via mass spectrometry for each antigen and inserted these sequences into the same *E. coli* expression vector. Purified protein from each VHH clone was then tested for binding to the desired antigen. A small-scale trial of binding of mWasabi to individual clones identified via mass spectrometry is illustrated in FIG. 9, with quantitation of binding capacity shown in FIG. 10. Typically the top several hits identified via mass spectrometry were the most likely to be true antigen-specific VHH clones.

What claim:

1. A method for generating pharmaceutical batches comprising antibodies or antibody fragments specific for an immunogen, the method comprising expressing ex vivo a plurality of antibody variable regions encoded by DNA identified or selected from antibody variable region gene sequence information from genomic DNA of antibody-producing cells of a host animal immunized with the immunogen; which identification or selection does not comprise physical screening; wherein immunization of the host animal comprises presenting the immunogen in cells originated from the host animal or cells from the same species as the host animal; wherein said cells originated from the host animal or cells from the same species as the host animal are transfected to express the immunogen.

2. The method of claim 1, wherein the antibodies or antibody fragments comprise VHH from heavy-chain only antibodies in camelidae or nurse shark animals.

3. The method of claim 1, wherein antibody variable gene sequence information is obtained by deep sequencing.

4. The method of claim 1, wherein the percentage of each variable region is ranked and the top 30% in abundance are chosen as immunogen-specific antibodies or antibody fragments.

5. A method for identifying immunogen-specific antibodies or antibody fragments through obtaining from an immunized host animal a library of nucleic acid sequence information of antibody variable region nucleotide sequences from genomic DNA, and a library of antibody variable region amino acid sequence information from antibody variable region proteins in serum, then combining the library of nucleic acid sequence information and the library of amino acid sequence information in identifying the immunogen-specific antibodies or antibody fragments; which method does not comprise physical screening; wherein immunization of the immunized host comprises presenting the antigen immunogen in cells originated from the host animal or cells from the same species as the host animal.

6. The method of claim 5, wherein the antibody variable region sequence information is from analyzing the antibody amino acid sequences by MASS spectrometry.

7. The method of claim 6, wherein the antibody or antibody fragments are prepared from serum of an immunized animal.

8. The method of claim 6, wherein the antibody or antibody fragments are prepared by expressing antibody-encoding gDNAs in a host cell.

9. A method of generating pharmaceutical batches comprising T cell receptors specific for an immunogen, the method comprising expressing ex vivo a plurality of T cell receptor variable regions encoded by DNA identified or selected from T cell receptor variable region gene sequence information from genomic DNA of T cell receptor-producing cells of a host animal immunized with the immunogen; which identification or selection does not comprise physical screening; wherein immunization comprises presenting the immunogen in cells originated from the host animal or cells from the same species as the host animal; wherein said cells originated from the host animal or cells from the same species as the host animal are transfected to express the immunogen.

10. The method of claim 1, wherein the immunogen is expressed by fibroblasts administered to the host.

11. The method of claim 4, wherein the top 25% in abundance of the variable gene sequences are chosen as immunogen-specific antibodies or antibody fragments.

12. The method of claim 4, wherein the top 15% in abundance of the variable gene sequences are chosen as immunogen-specific antibodies or antibody fragments.

13. The method of claim 4, wherein the top 10% in abundance of the variable gene sequences are chosen as immunogen-specific antibodies or antibody fragments.

14. The method of claim 4, wherein the top 5% in abundance of the variable gene sequences are chosen as immunogen-specific antibodies or antibody fragments.

15. The method of claim 1, wherein the antibody variable regions from genomic DNA are not amplified.

16. The method of claim 1, wherein the expressed antibody variable regions comprise affinity purification tags.

17. The method of claim 9, wherein the immunogen is expressed by fibroblasts administered to the host.

18. The method of claim 1, wherein presenting the immunogen in cells originated from the host or cells from the same species as the host comprises transfecting the cells originated from the host or cells from the same species as the host with mRNA that expresses the immunogen.

19. The method of claim 9, wherein presenting the immunogen in cells originated from the host or cells from the same species as the host comprises transfecting the cells originated from the host or cells from the same species as the host with mRNA that expresses the immunogen.

* * * * *